United States Patent [19]

Millar et al.

[11] Patent Number: 4,820,859

[45] Date of Patent: Apr. 11, 1989

[54] PROCESS FOR THE PRODUCTION OF HIGH ENERGY MATERIAL

[75] Inventors: Ross W. Millar, Hertford; Norman C. Paul, Hoddesdon; David H. Richards, Waltham Abbey, all of United Kingdom

[73] Assignee: Secretary of State for Defence in Her Majesty's Government of the United Kingdom, London, United Kingdom

[21] Appl. No.: 794,340

[22] Filed: Nov. 5, 1985

Related U.S. Application Data

[63] Continuation of Ser. No. 507,170, Jun. 27, 1983, abandoned.

[30] Foreign Application Priority Data

Jul. 15, 1982 [GB] United Kingdom ................. 8220082

[51] Int. Cl.$^4$ .............................................. C07C 77/02
[52] U.S. Cl. ................................ 558/483; 525/333.2; 525/377; 558/484; 558/485; 558/487; 558/480
[58] Field of Search ............... 558/480, 484, 483, 485, 558/487; 525/333.2, 377

[56] References Cited

U.S. PATENT DOCUMENTS

| 2,539,824 | 1/1951 | Garber et al. ........................ 525/377 |
| 3,249,631 | 5/1966 | Soffer ................................. 149/88 X |
| 3,549,687 | 12/1970 | Bachman et al. ..................... 558/480 |
| 3,583,961 | 6/1971 | Magay et al. ........................ 525/377 |
| 3,583,962 | 6/1971 | Magay ................................. 525/377 |
| 3,631,110 | 12/1971 | Smetana .............................. 558/480 |
| 3,721,698 | 3/1973 | Stogryn et al. ...................... 558/487 |
| 4,059,719 | 11/1977 | Blaha et al. ......................... 525/377 |
| 4,138,535 | 2/1979 | Schweiger ........................... 260/466 |

FOREIGN PATENT DOCUMENTS

| 448719 | 5/1948 | Canada ................................. 260/467 |
| 455530 | 3/1949 | Canada ................................. 260/467 |
| 911759 | 6/1946 | France ................................... 149/88 |
| 1100372 | 9/1955 | France . |

OTHER PUBLICATIONS

Nichols et al., J. Am. Chem. Soc., vol. 75, pp. 4255 to 4258, (1953), (QD1A5).
Lane, J. Chem. Soc., (London), pp. 1172 to 1175 (1953).
English Translation of French Patent 1,100,372 of Boileau.
Kirk—Othmer, Encyclopedia of Chemical Technology, 3rd Edition, vol. 9, pp. 572-585.
Chemical Abstracts, vol. 84, No. 15, (Apr. 12, 1876), also #105306s.

*Primary Examiner*—Edward A. Miller
*Attorney, Agent, or Firm*—Cushman, Darby & Cushman

[57] ABSTRACT

A process for the production of a high energy material involves reacting, in an inert organic solvent, a heterocyclic compound selected from oxirane, aziridine, oxetane or azetidine with a nitrogen oxide selected from dinitrogen tetroxide ($N_2O_4$) and dinitrogen pentoxide ($N_2O_5$) and, when the nitrogen oxide is $N_2O_4$, oxidizing the O- or N- nitroso substituent or substituents in the product obtained to O- or N- nitro substituent or substituents. The heterocyclic compounds may be substituents or unsubstituted. In the former case the preferred substituents groups are halogen, alkyl, alkenyl, nitro and epoxy (as in epoxidized polybutadiene). The solvent is preferably a chlorinated alkane.

Novel nitrated derivatives of polybutadiene, in which between 1% and 25% of the carbon atoms in the polymer are substituted by nitrate ($ONO_2$), are also provided. These novel materials are liquid rubbers when the polybutadiene starting material has a molecular weight between 2000 and 10000.

15 Claims, No Drawings

PROCESS FOR THE PRODUCTION OF HIGH ENERGY MATERIAL

This is a continuation of application Ser. No. 507,170, filed June 27, 1983, which was abandoned upon the filing hereof.

The present invention relates to a process for the production of high energy materials, to high energy materials produced thereby and to certain novel high energy materials.

At present the manufacture of the group of high energy materials which contain nitrate (O - nitro) substituents or the analogous materials which contain a mixture of O - nitro substituents generally requires the use of strong mineral acids (especially $HNO_3/H_2SO_4$ mixtures) and high temperatures. These conditions present the manufacturer of these materials with a number of problems which he must overcome if the method of production is to meet modern standards of safety. These problems include the control, containment and disposal of a highly dangerous and corrosive reaction mixture (hot mineral acids).

It is one object of the present invention to overcome at least some of the above problems by providing a process for the production of certain high energy materials (especially those which contain O - nitro substituents but also those which contain O - nitro and N - nitro substituents) which proceeds effectively at ambient temperature (0°-30° C.), employs inert organic solvents, and does not require the disposal of strong mineral acids.

Other objects and advantages of the present invention will become apparent from the following description thereof.

According to the present invention a process for the production of a high energy material comprises reacting, in an inert organic solvent, a heterocyclic compound selected from the group oxirane (ethylene oxide), aziridine, oxetane and azetidine with a nitrogen oxide selected from the group dinitrogen tetroxide ($N_2O_4$) and the dinitrogen pentoxide ($N_2O_5$) and, when the nitrogen oxide is dinitrogen tetroxide, oxidising the O - or N - nitroso substituent or substituents in the product obtained to O - or N - nitro substituent or substituents.

In the present specification each of the terms oxirane, aziridine, oxetane and azetidine encompasses both the unsubstituted compounds and the substituted derivatives of the compounds. In the latter case the heterocyclic ring may be substituted by any substituent group. Preferably however the substituent group is at least one of the following halogen, alkyl, alkenyl, nitro and epoxy (as in butadiene diepoxide or the epoxidised form of a polybutadiene), although other groups, such as aldehydo, amino, amido, acyl, carboxylate ester, carboxylic acid, hydroxy, alkoxy, aryl and alkyne, may either additionally or alternatively be present.

The reaction, between heterocyclic compound and nitrogen oxide, is conducted in an inert organic solvent. Any anhydrous organic solvent which does not react with either the starting materials or the reaction products of the present process may be employed. Preferably, however, it should also be possible to either dispose of or recycle the solvent, simply, safely and at little cost. The chlorinated alkanes, dichloromethane, chloroform and carbon tetrachloride, generally meet these criteria and are therefore preferred.

The present process may be conducted at high temperature (up to the boiling point of the solvent) and/or pressure. It is preferred, however, to allow the reaction to proceed at ambient temperature (0°-30° C., especially 10°-20° C.) and pressure.

When the present heterocyclic compounds are reacted with dinitrogen pentoxide the required high energy materials are obtained without further treatment of the reaction mixture. However, when the present heterocyclic compounds are reacted with dinitrogen tetroxide the required high energy materials are only obtained after subsequent oxidation of the resultant O - or N - nitroso compounds. This oxidation step may be performed by any oxidising agent that transforms an O or N - nitroso substituent into an O - or N - nitro substituent provided that the agent has no effect on any other part of the nitroso compound (eg does not oxidise a double bond or hydrolyse a halo substituent). In many cases the preferred oxidising agent is ozone.

Generally the present process proceeds very quickly at ambient temperature and pressure. In a few cases, however, the process, as described above, may be rather slow and it may be necessary to increase the rate of reaction. This may be done by increasing the reaction temperature to above the ambient; alternatively the reaction may be controlled by the presence of a Lewis acid such as aluminium chloride or stannic chloride.

Although some of the products of the present process are known compounds, in a further aspect of the present invention there is provided a novel group of nitrated polymers. More specifically there is provided a nitrated polybutadiene, especially a hydroxy-terminated polybutadiene, in which between 1% and 25%, especially between 5% and 20%, of the carbon atoms in the polymer are substituted by nitrate ($ONO_2$) groups. These novel materials are liquid rubbers when the polybutadiene starting material (prior to nitration) has a molecular weight between 2000 and 10000.

The present process will now be described by way of example only.

Preparation of Dinitrogen Pentoxide ($N_2O_5$)

$N_2O_5$ may be prepared by the oxidation of dinitrogen tetroxide ($N_2O_4$) with ozone. Because of the thermal instability of $N_2O_5$, during the preparation and subsequent use the temperature should not exceed 30° C. and preferably operations are carried out between 0° and 20° C. All operations must be carried out under anhydrous conditions since $N_2O_5$ is readily hydrolysed to nitric acid. For the reactions described here it is convenient to dissolve the $N_2O_5$ in an inert solvent, such as a chlorinated alkane.

An ozone/oxygen mixture, from a commercially available ozoniser was passed into a glass vessel containing $N_2O_4$. Oxidation occurs in the gas phase and the resulting $N_2O_5$ is carried in the oxygen stream and trapped in a series of cold traps kept at $-20°$ to $-30°$ C. Any unreacted $N_2O_4$ is subsequently reacted by resubliming the initial trapped product in an ozonised oxygen stream. The pure, white crystals of $N_2O_5$ can be stored at $-78°$ C. for at least 7 days before use without any noticeable decomposition.

Dinitrogen Tetroxide ($N_2O_4$)

$N_2O_4$ was obtained commercially as a compressed gas and was used in the following examples directly from a cylinder.

Reactions of Nitrogen Oxides with Heterocyclic Compounds General Procedures

A. Reaction with $N_2O_5$

A solution of $N_2O_5$ in an inert solvent was prepared. The heterocyclic compound, dissolved in the same solvent, was added to the stirred $N_2O_5$ solution in an equimolar amount. The reaction was immediate and generally carried out at or below room temperature in order to minimise the thermal decomposition of $N_2O_5$ and in some cases to avoid losses of the reacting compound where it's volatility was high. Precautions were taken to avoid hydrolysis of the $N_2O_5$ by atmospheric water vapour. Any excess acidity was removed by stirring with solid sodium hydrogen carbonate and the product was isolated by vacuum distillation of the solvent.

B. Reaction with $N_2O_4$ and subsequent oxidation of the product

A solution of $N_2O_4$ was prepared by absorption of the gas into a dry inert solvent and the heterocyclic compound was added in an equimolar amount to this stirred solution. The reaction mixture was stirred at room temperature for 30 mins and the resultant product (a nitrite - nitrate ester) was oxidised, in situ, with an anhydrous oxidising agent, for example ozone. After removal of any excess acidity with sodium hydrogen carbonate the product was isolated by vacuum distillation of the solvent.

Specific Examples

1. Ethylene Oxide

Ethylene oxide was reacted with $N_2O_5$ using the general procedure (A) described above. The product was the dinitrate ester of ethylene glycol ($O_2NOH_2C\ CH_2ONO_2$). In some runs small amounts of ethylene glycol mononitrate were observed through the reaction of traces of nitric acid with ethylene oxide.

Ethylene oxide has also been reacted with $N_2O_4$ and subsequently oxidised with ozone, general procedure (B) above. The product of this reaction is also the dinitrate ester of ethylene glycol.

2. Propylene oxide

Propylene oxide was reacted with $N_2O_5$ as described in general procedure (A) to yield propylene glycol dinitrate ($CH_3CH(ONO_2)CH_2ONO_2$).

3. Epichlorohydrin

Reaction of epichlorohydrin with $N_2O_5$, general procedure (A), gave 1 - chloro - 2, 3 - propanediol dinitrate ($ONO_2CH_2CH\ (ONO_2)CH_2Cl$).

4. Butadiene Monoepoxide

Butadiene monoepoxide was reacted with $N_2O_5$ as described above in general procedure (A). The product was 3, 4 - butenediol dinitrate, ($CH_2=CHCH(ONO_2)CH_2ONO_2$).

5. Butadiene Diepoxide

Butadiene diepoxide was reacted with $N_2O_5$ as described in general procedure (A) except that the nitrogen oxide was added to the epoxide. This reaction gave mainly 1, 2 - epoxy-3, 4 -butanediol dinitrate, although some polymeric products were also produced.

Reaction of 2 moles of $N_2O_5$ with 1 mole of butadiene diepoxide by the same procedure gave erythritol tetranitrate ($O_2NOCH_2CH(ONO_2)CH(ONO_2)CH_2ONO_2$).

6. Epoxidised Polybutadiene

A commercially available hydroxy terminated polybutadiene was epoxidised by known procedures to give partially epoxidised materials where the degree of epoxidation ranged from 10 to 50% of the theoretical maximum. Solutions of these materials were reacted with an amount of $N_2O_5$ equivalent to the degree of epoxidation by the method of general procedure (A). The resulting polymers contained nitrate ester groups. The materials were liquid rubbers.

7. Aziridine

Reaction of aziridine with $N_2O_5$, general procedure (A), gave N - nitroethanolamine nitrate, ($O_2NNHCH_2CH_2ONO_2$) as a component of the product.

8. Oxetane

Reaction of oxetane with $N_2O_5$, as described in general procedure (A), gave 1, 3 - propanediol dinitrate ($O_2NO(CH_2)_3\ ONO_2$).

9. 3, 3 - Dimethyloxetane

Reaction of 3, 3 - dimethyl oxetane with $N_2O_5$, as described in general procedure (A), gave 2, 2 - dimethyl - 1, 3 -propanediol dinitrate.

10. 3, 3 - Pentamethylene oxetane

Reaction of 3, 3 - pentamethyleneoxetane with $N_2O_5$, as described in general procedure (A), gave 2, 2 - pentamethylene -1, 3 - propanediol dinitrate.

What I claim is:

1. A process for the production of a high energy material comprising:
    (a) reacting, in an inert organic solvent, a heterocyclic compound selected from the group oxirane, aziridine, oxetane and azetidine with a nitrogen oxide selected from the group dinitrogen tetroxide ($N_2O_4$) and dinitrogen pentoxide ($N_2O_5$) to afford, when the nitrogen oxide is $N_2O_4$, a product A containing O - nitro and O-nitroso substituents or a product B containing O - nitro and N - nitroso substituents, and, when the nitrogen oxide is $N_2O_5$, a product C containing 0 - nitro substituents or a product D containing O - nitro and N - nitro substituents,
    (b) when the nitrogen oxide is $N_2O_4$, oxidising product A to product C or product B to product D by treating product A or product B with ozone, and
    (c) isolating either product C or product D.

2. A process according to claim 1 wherein the heterocyclic compound is substituted by at least one group selected from halogen, alkyl, alkenyl, nitro and epoxy.

3. A process according to claim 1 wherein the inert organic solvent comprises a medium selected from dichloromethane, chloroform and carbon tetrachloride.

4. A process according to claim 1 comprising reacting the heterocyclic compound and the nitrogen oxide in the presence of a Lewis acid.

5. A process according to claim 1 wherein the heterocyclic compound comprises an epoxidised polybutadiene.

6. A process according to claim 5 wherein the heterocyclic compound comprises an epoxidised hydroxy-terminated polybutadiene.

7. A process according to claim 1 wherein the heterocyclic compound comprises ethylene oxide, propylene oxide, epichlorohydrin, butadiene monoepoxide, butadiene diepoxide, aziridine, oxetane, 3, 3 - dimethyloxetane or 3, 3 - pentamethyleneoxetane.

8. A process for the production of a high energy material comprising
    (a) reacting, in an inert organic solvent, a heterocyclic compound selected from the group oxirane, aziridine, oxetane and azetidine and the substitued derivatives thereof with dinitrogen pentoxide (N₂O₅) to afford either a product C containing O-nitro substituents or a product D containing O-nitro and N-nitro substituents, and (b) isolating either product C or product D.

9. A process according to claim 8 wherein the heterocyclic compound is substituted by at least one group selected from halogen, alkyl, alkenyl, nitro and epoxy.

10. A process according to claim 8 wherein the inert organic solvent comprises a medium selected from dichloromethane, chloroform and carbon tetrachloride.

11. A process according to claim 8 comprising oxidizing product A to product C or product B to product D by treating product A or product B with ozone.

12. A process according to claim 8 comprising reacting the heterocyclic compound and the nitrogen oxide in the presence of a Lewis acid.

13. A process according to claim 8 wherein the heterocyclic compound comprises an epoxidized polybutadiene.

14. A process according to claim 13 wherein the heterocyclic compound comprises an epoxidized hydroxy-terminated polybutadiene.

15. A process according to claim 8 wherein the heterocyclic compound comprises ethylene oxide, propylene oxide, epichlorohydrin, butadiene monoepoxide, butadiene diepoxide, aziridine, oxetane, 3,3-dimethyloxetane or 3,3-pentamethyleneoxetane.

* * * * *